United States Patent
Salganicoff et al.

[11] Patent Number: 6,055,322
[45] Date of Patent: Apr. 25, 2000

[54] METHOD AND APPARATUS FOR ILLUMINATING AND IMAGING EYES THROUGH EYEGLASSES USING MULTIPLE SOURCES OF ILLUMINATION

[75] Inventors: Marcos Salganicoff, Philadelphia, Pa.; Keith James Hanna, Princeton, N.J.

[73] Assignees: Sensor, Inc., Moorestown; Sarnoff Corporation, Princeton, both of N.J.

[21] Appl. No.: 08/980,684

[22] Filed: Dec. 1, 1997

[51] Int. Cl.[7] ........................................... G06K 9/00
[52] U.S. Cl. ............................. 382/117; 351/206
[58] Field of Search .................... 382/117, 115, 382/118, 217, 218, 278, 291, 190; 348/78; 351/205, 206, 211, 213, 215

[56] References Cited

U.S. PATENT DOCUMENTS

| | | | |
|---|---|---|---|
| 4,641,349 | 2/1987 | Flom et al. | 382/117 |
| 5,291,560 | 3/1994 | Daugman | 382/117 |
| 5,572,596 | 11/1996 | Wildes et al. | 382/117 |

FOREIGN PATENT DOCUMENTS

WO 86/05018  8/1986  WIPO  ............................... G06K 9/00

OTHER PUBLICATIONS

"Iris Recognition Technology" by Gerald O. Williams, *IEEE AES Systems Magazine*, Apr., 1997, pp. 23–29.

"Polarization–Based Material Classification from Specular Reflection" by Lawrence B. Wolff, *IEEE Transaction on Pattern Analysis and Machine Intelligence*, 12 (1990), Nov. No. 11.

*Primary Examiner*—Amelia Au
*Assistant Examiner*—Jingge Wu
*Attorney, Agent, or Firm*—Buchann Ingersoll, P.C.

[57] ABSTRACT

A reliable method of illuminating and imaging an eye through eyeglasses uses a carefully selected subset of multiple monochromatic light sources, a camera with an imager that exhibits minimal blooming, and a narrow-bandwidth optical bandpass filter to filter out most of the ambient illumination while passing most of the light from the system's own illuminator.

16 Claims, 1 Drawing Sheet

METHOD AND APPARATUS FOR ILLUMINATING AND IMAGING EYES THROUGH EYEGLASSES USING MULTIPLE SOURCES OF ILLUMINATION

FIELD OF THE INVENTION

The invention relates to identifying individuals from facial images, and more particularly from images of the eye.

BACKGROUND OF THE INVENTION

There are several methods known as biometrics for recognizing or identifying an individual from personal biological characteristics. Some of these methods involve imaging of the face or eye and analyzing the facial features, retinal vascular patterns of the eye, or patterns in the iris of the eye. In recent years there has been a demand for more reliable systems to identify individuals, particularly those persons who desire access to a secured area or system. A common example of such a secured system are automated teller machines which allow authorized users to conduct banking transactions. Many of these systems are used by a wide variety of people. Very often these people demand quick as well as accurate identification.

A technique for accurately identifying individuals using iris recognition is described in U.S. Pat. No. 4,641,349 to Flom et al. and in U.S. Pat. No. 5,291,560 to Daugman. The systems described in these references require clear, well-focused images of the eye. The presence of eyeglasses tends to interfere with good eye images because of reflections on the eyeglasses. Contact lenses may also cause reflections that interfere with eye imaging. However, because contact lenses have a greater curvature than eyeglasses reflections from contact lenses are smaller and less of a problems than reflections from eyeglasses.

Reflections may come from the system's own illumination. In this case, calculations show that the irradiance (illuminance for visible light) at the camera lens from the specular reflection of an illuminator from eyeglasses is on the order of 1000 times greater than the irradiance at the camera of the image of the eye caused by diffuse reflection of the illuminator. A camera viewing the eye must have a combination of lens, aperture, and exposure time that will result in a sufficiently bright image of the eye. Thus, the much brighter specular reflection of the illuminator will saturate the picture elements (pixels) of the camera's image sensor that cover the area of the specular reflection, and all information about the portion of an eye image obscured by this reflection will be lost. Furthermore, the values of pixels surrounding the area of the specular reflection may be corrupted by the saturated pixels in a phenomenon called "blooming". This occurs because the pixels of charge-coupled devices (CCD's), the most common electronic imagers, are not well isolated from one another.

Reflections may also come from ambient illumination, such as bright sunlight. The irradiance generated by such reflections depends on specific ambient conditions, but the power of direct sunlight is comparable to or greater than the power of any safe artificial illuminator, therefore ambient illumination can sometimes cause the same kind of obscuring reflection as the system's own artificial illuminator.

It is possible to ask the subject to remove his or her eyeglasses in order to get a good image of the subject's eye. However, this is potentially annoying, and the subject may refuse to remove the glasses, or avoid using the system. Consequently, there is a need for an imaging system that can obtain useful images of the eye while minimizing the effect of specular reflections without requiring the subject to remove any eyeglasses or contact lenses that may be present.

SUMMARY OF THE INVENTION

We provide a reliable method and apparatus for illuminating and imaging an eye through eyeglasses or contact lenses. First we select multiple light sources with relatively wide spacing from one another. We turn off one or more of the light sources which cause specular reflections on the eyeglasses that obscure the camera's view of the iris. We may use a camera with an imager that has high isolation between adjacent pixels and thus minimal blooming, in contrast to the commonly used standard CCD imager. We may further choose the light source to be monochromatic, or nearly monochromatic with a narrow spectral bandwidth, with a center wavelength in the range of 700 to 800 nanometers for balance of visibility, imager sensitivity, and iris absorption properties. We may also use a narrow-bandwidth optical bandpass in front of the imager in the camera. This filter has a center wavelength and bandwidth matching the light sources to filter out most of the ambient illumination while passing most of the light from the system's own illuminators.

DESCRIPTION OF THE PREFERRED EMBODIMENTS

Figure 1:
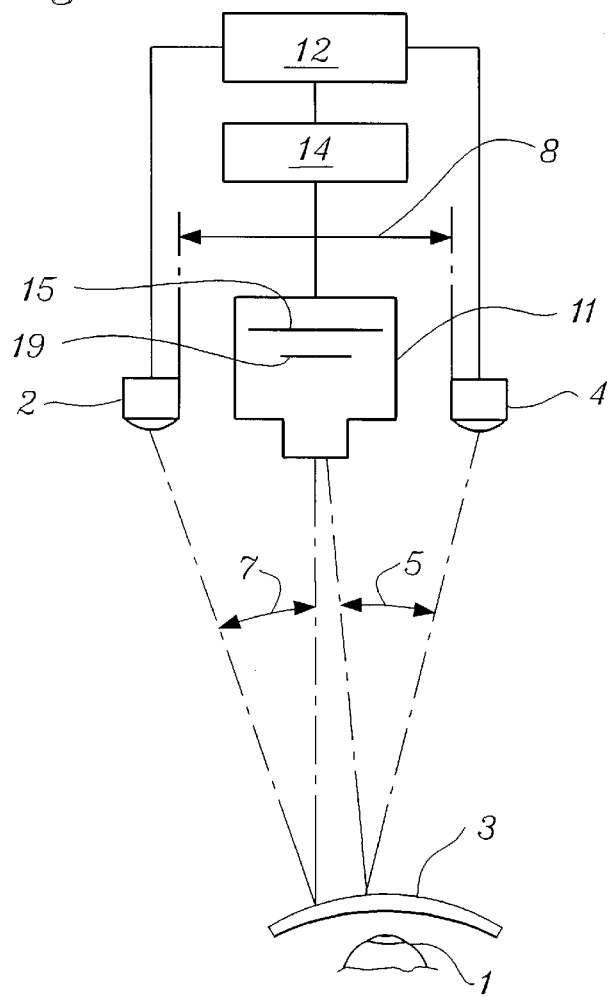
FIG. 1 is a diagram showing a preferred embodiment of the present invention in which two light sources are used to illuminate an eye behind an eyeglass lens for imaging by a camera that is synchronized to the two light sources.

In FIG. 1, we show a diagram of the top view of a preferred embodiment of the present invention. The eye 1 of a subject with eyeglass lens 3 is looking into a camera 11. The eye is illuminated by a light source 2 and a light source 4. The emission patterns of the light sources 2 and 4 are such that either of them generates illumination that is fairly even across the front surface of the eye 1 with sufficient intensity for the camera 11 to record a good image of the eye 1.

Instead of leaving the light sources 2 and 4 on during the time that a subject is present, the light sources 2 and 4 are pulsed or flashed in synchronization with the exposure times of the camera 11. This can be done using a strobing device 12 and an illumination controller 14 connected to the strobing device 12 and the camera 11. Both the intensity and duration of these pulses are controlled to get the correct exposure of the images of the eye 1. This allows the radiation exposure of the eye 1 to be kept well below internationally accepted safety limits, while still providing sufficient illumination.

Figure 2:
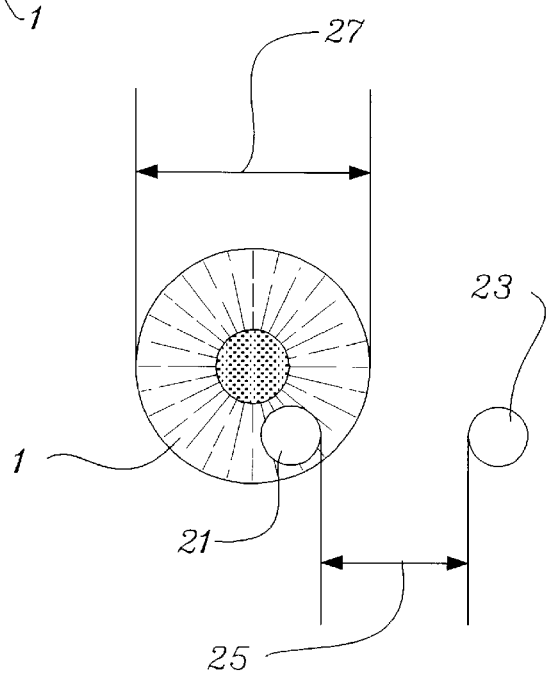
FIG. 2 is a view of an eye as seen by a imaging camera through an eyeglass lens with the view of the iris partially obscured by specular reflection of illuminating light sources.

At least one light path 7 from a light source 2 to the camera 11 produces a specular reflection from a first surface (front or back) of the eyeglass lens 3 and thus generates a virtual image 23 of the light source 2 that is visible to the camera 11 as seen in the camera's view illustrated in FIG. 2. Similarly, at least one light path 5 from a light source 4 to the camera 11 produces a specular reflection from the same first surface of the eyeglass lens 3 and thus generates a virtual image 21 of the light source 4 that is visible to a camera 11 as seen in the camera's view of an eye 1 illustrated in FIG. 2. Since the virtual image 21 obscures the iris portion of the eye 1 in FIG. 2, the controller 14 will turn off the light source 4 which causes the virtual image 21, while continuing to activate the light source 2, during exposure of a succeeding image taken immediately after the image shown in FIG. 2. Assuming minimal movement of the subject during the time between the image of FIG. 2 and the succeeding image, the succeeding image will show an image of the eye 1 illuminated by the light source 2 without the virtual image 21 from the light source 4 obscuring the iris. It will always be possible to turn off one source to remove specular reflections obscuring the iris image so long as the apparent separation distance 25 between the virtual images 21 and 23 is greater than the iris diameter 27. Under this constraint, only one of the two virtual images 21 and 23 can obscure the iris in any single image.

The apparent separation distance 25 depends on the curvature of the lens surface causing the reflections and the separation distance 8 between the light sources 2 and 4 in FIG. 1. Since the surfaces of modem eyeglass lenses are generally curved outward from the eye as shown in the drawing of eyeglass lens 3, these surfaces act as convex mirrors, and the apparent separation distance 25 will decrease as the curvature of the eyeglass lens surface increases causing the reflections to increase. For a given curvature of the eyeglass lens surface causing the reflections, the separation distance 25 will increase as the separation distance 8 is increased. By researching the distribution of curvature in modem eyeglasses, we may choose a separation distance 8 such that the separation distance 25 is greater than the iris diameter 27, which is typically 10–12 millimeters, for a given percentage of the eyeglass-wearing population. In the present embodiment, we choose a separation distance 8 of from 25 to 35 centimeters, preferably about 30 centimeters, which causes the separation distance 25 to be greater than the iris diameter 27 for more than 95% of the eyeglass-wearing population.

Although FIG. 2 shows only one pair of virtual images 21 and 23 caused by a first surface of an eyeglass lens 3, the second surface of the lens will normally cause another pair of virtual images. These images act much the same as the images caused by the first surface. The pair of images caused by the surface of the eyeglass lens 3 having the greatest curvature (smallest radius) will have the smallest separation distance 25, and this surface will thus determine the desired separation distance 8.

The light sources 2 and 4 may be implemented with one or more high-power light-emitting diodes (such as the OD-669 IR LED array manufactured by Opto-Diode Corporation), a laser diode fed through an optical fiber, a laser fitted with a diverging lens, an incandescent lamp, or any other source that produces sufficient power with appropriate emission pattern in the appropriate spectral band.

The virtual images 21 and 23 from the specular reflection off of the eyeglass lens 3 are so bright that they generally saturate some of the pixels of the imager 15 in the camera 11. This saturation distorts the values of the pixels immediately surrounding the image of the specular reflection of either of the sources 2 or 4 in a phenomenon called "blooming" when the imager 15 is a charge-coupled device (CCD), the most common type. Newer CMOS (complementary metal-oxide semiconductor) or CID (Charge-Injection Device) imagers have much more electrical isolation between adjacent pixels than the CCD's, minimizing blooming. Because of the minimal blooming we prefer to provide a CMOS imager 15, such as the VLSI Vision VV5850, instead of the more common CCD imager, in order to mitigate negative effects of saturated virtual images of illumination sources, such as virtual image 23 in the current description, that do not obscure the iris but may still distort nearby pixels, some of which may be part of the iris image. There may be other imagers with high resistance to blooming available or developed in the future that could be used in place of a standard CCD imager.

The preferred embodiment of FIG. 1 shows two light sources 2 and 4 arranged horizontally. However, two or more light sources may be arranged horizontally, vertically, radially, or in any other geometry so long as the spacing of the light sources is sufficient for the virtual images of the sources reflected from an eyeglass lens in the camera's view of an eye to be separated far enough so that the illumination controller can turn off all of the sources obscuring the iris while having enough sources still active to properly illuminate the eye for a good image.

All of the methods and apparatus described above will work for any wavelength of illumination from light sources 2 and 4 for which the imager 15 has sufficient sensitivity. CMOS, CCD, and other silicon-based imagers have relatively high sensitivity in the range of about 500–800 nanometers with sensitivity dropping off to near zero at about 300 nanometers on the low end and about 1050 nanometers on the high end.

In order to minimize the effect of ambient illumination, it is desirable for the illumination from the light sources 2 and 4 to have a narrow spectral bandwidth so that a narrow optical bandpass filter 19 may be used in the camera to allow the imager 15 to see illumination from the light sources 2 and 4 while not being able to see light at any other wavelengths. For example, the light sources 2 and 4 may be implemented with lasers having center wavelengths of 750 nanometers and spectral bandwidths of less than 10 nanometers. This would enable the use of a thin-film interference bandpass filter 19 with the same center wavelength and a 10-nanometer bandwidth. In the preferred embodiment of FIG. 1, the filter 19 is immediately in front of the imager 15 in the camera 11 because the center wavelength of the filter 19 is somewhat dependent on the angle of incidence of the light to be filtered. With proper optical design, there will be a location immediately in front of the imager 15 where all of the light going to the imager 15 will pass through the filter 19 at near normal angle of incidence.

The sun is very likely the worst case of interfering ambient illumination. At 750 nanometers, the worst case solar spectral irradiance is about 100 milliwatts per square centimeter per micron of spectral band. Within the 10-nanometer bandwidth of the filter 19, only 1 milliWatt per square centimeter of the sun's irradiance will be detectable by the imager 15. This level is less than or equal to the level of irradiance that the light source 2 produces at the eye 1. Thus the controlled illumination from the light sources 2 and 4 is not overwhelmed by illumination from the sun even in worst-case sunny conditions.

The preceding example of illumination at 750 nanometers is also a good choice of wavelength because human eyes cannot see wavelengths greater than about 700–750 nanometers. In order that the imaging of the eye 1 be unobtrusive to the subject, it is desirable that the subject not be able to see much of the illumination from the light sources 2 and 4.

When the iris portion of the eye is used for identification, it is important to be able to separate the iris portion from the rest of the eye image. Images of the eye taken with wavelengths of about 840–920 nanometers show a relatively low contrast between the brightness of the iris and the brightness of the surrounding sclera (the white of the eye) making the outer boundary of the iris difficult to locate. Biomedical research shows that the function of incident light absorption by the iris versus wavelength has a sharp drop at about 750–800 nanometers. Therefore, use of a wavelength of illumination of 750 nanometers or below, as in the example above, will increase the absorption by the iris and make the iris appear darker, thus improving the contrast between the iris and the sclera.

In summary, we prefer for the present invention to use a monochromatic, or nearly monochromatic, illumination with center wavelength in the range of 700–800 nanometers to balance the considerations of visibility to the subject, sensitivity of the imager 15, and contrast along the iris/sclera boundary.

We have described the present invention as used for imaging the eye. However, there are other applications for this invention in which an image is taken of an object that is behind a lens or other light transmissive curved structure. For example, this method and apparatus could be used to obtain images of products packaged in light transmissive packaging such as glass jars or blister packages. Such images could be used for quality control or product identification purposes.

The light transmissive structure is not limited to clear materials. That structure may allow passage of limited wavelengths of light which could be visible or invisible to the human eye. A common example of such a structure are the plastics used in sunglasses.

Although we have shown certain present preferred embodiments of our invention, it should be distinctly understood that the invention is not limited thereto, but may be variously embodied within the scope of the following claims.

We claim:

1. A method for imaging an area of an object positioned behind a light transmissive structure using illuminators which produce specular reflections on the light transmissive structure wherein at least an approximate diameter of the area to be imaged is known comprising:
   a. providing first and second illuminators positioned a distance apart from one another which is not less than the known at least approximate diameter; such that a distance between the specular reflections on the transmissive structure due to each illuminator are not less than the at least an approximate diameter of the area on the object to be imaged;
   b. illuminating the area with the first illuminator and checking to see if the illuminator has produced a specular reflection that obscures the area of the object;
   c. if the first illuminator has produced a specular reflection that obscures the area of the object then illuminating the area with the second illuminator;
   d. obtaining an image of the area while the first illuminator is on if the first illuminator has produced a specular reflection that has not obscured the area; and
   e. obtaining an image of the area while the second illuminator is on if the first illuminator has produced a specular reflection that has obscured the area.

2. The method of claim 1 wherein the illuminators produce light that is visible to a human eye.

3. The method of claim 1 wherein the illuminators produce light that is invisible to a human eye.

4. The method of claim 3 wherein the illuminators produce infrared light.

5. The method of claim 1 wherein the object is an eye, the area is an iris and the light transmissive structure is eyeglasses.

6. The method of claim 1 wherein the image is obtained using a camera having a nonblooming imager.

7. The method of claim 6 wherein the imager is a CMOS device.

8. The method of claim 1 also comprising the step of filtering light after that light has been reflected from the object.

9. The method of claim 8 wherein the filtering removes light produced by ambient illumination.

10. The method of claim 1 wherein the illuminators produce monochromatic light.

11. The method of claim 1 wherein the illuminators produce light having wavelengths between 700 and 800 nanometers.

12. The method of claim 1 wherein the light transmissive structure is a product package.

13. The method of claim 1 wherein the product package is a glass jar.

14. The method of claim 1 wherein the product package is a blister package and the light transmissive structure is a blister.

15. The method of claim 1 where in the illuminators produce light having wavelenghts below 750 nanometers.

16. The method of claim 1 wherein the first illimunator is spaced 25 to 35 centimeters from the second illuminator.

* * * * *